United States Patent
Biber et al.

(10) Patent No.: US 10,132,885 B2
(45) Date of Patent: Nov. 20, 2018

(54) ARCHITECTURE FOR CASCADED SIGNAL SELECTION AND SIGNAL CONCENTRATION AND/OR REDUCTION OF DIGITAL RECEIVED DATA BY DECIMATION AND CHANNEL PRESELECTION

(71) Applicants: Stephan Biber, Erlangen (DE); Georg Pirkl, Dormitz (DE)

(72) Inventors: Stephan Biber, Erlangen (DE); Georg Pirkl, Dormitz (DE)

(73) Assignee: Siemens Aktiengesellschaft, München (DE)

( * ) Notice: Subject to any disclaimer, the term of this patent is extended or adjusted under 35 U.S.C. 154(b) by 484 days.

(21) Appl. No.: 14/975,779

(22) Filed: Dec. 19, 2015

(65) Prior Publication Data

US 2016/0195595 A1    Jul. 7, 2016

(30) Foreign Application Priority Data

Dec. 19, 2014 (DE) .......... 10 2014 226 676

(51) Int. Cl.
  *G01V 3/00* (2006.01)
  *G01R 33/36* (2006.01)
  (Continued)

(52) U.S. Cl.
  CPC .......... *G01R 33/3664* (2013.01); *A61B 5/704* (2013.01); *G01R 33/30* (2013.01); *G01R 33/3621* (2013.01)

(58) Field of Classification Search
  USPC ....................................................... 324/321
  See application file for complete search history.

(56) References Cited

U.S. PATENT DOCUMENTS 5,932,936 A    8/1999 Potthast et al.
6,943,548 B1 * 9/2005 Hertz ................. G01R 33/3621
                                                324/309
(Continued)

FOREIGN PATENT DOCUMENTS

CN    101103918 A    1/2008
CN    101581771 A    11/2009
(Continued)

OTHER PUBLICATIONS

German Office Action for German Application No. 10 2014 226 676.9, dated Jun. 29, 2015, with English Translation.
(Continued)

*Primary Examiner* — Rodney Fuller
(74) *Attorney, Agent, or Firm* — Lempia Summerfield Katz LLC

(57) ABSTRACT

A magnetic resonance tomography system includes a plurality of MRT plugs for connection of antenna elements, respectively, of one of a plurality of local coils. Due to at least one analog switch matrix, antenna elements respectively connected to fewer than all of the MRT plugs may be connected in an analog fashion to receive signal processing elements of one of a plurality of receive signal processing element blocks respectively having a plurality of receive signal processing elements. Between outputs of receive signal processing element blocks and an evaluation device of the magnetic resonance tomography system, a digital channel selection unit is provided. On an input side of the digital channel selection unit, the digital channel selection unit may be connected to antenna elements. Signals from fewer antenna elements are present at the output of the digital channel selection unit than at an input of the digital channel selection unit.

20 Claims, 10 Drawing Sheets

(51) Int. Cl.
*A61B 5/00* (2006.01)
*G01R 33/30* (2006.01)

(56) References Cited

U.S. PATENT DOCUMENTS

| | | | |
|---|---|---|---|
| 6,943,551 B2 | 9/2005 | Eberler et al. | |
| 6,977,502 B1* | 12/2005 | Hertz | G01R 33/3621 324/318 |
| 8,384,388 B2* | 2/2013 | Biber | G01R 33/3415 324/318 |
| 2003/0083568 A1* | 5/2003 | Frigo | G01R 33/3621 600/410 |
| 2009/0286478 A1 | 11/2009 | Biber et al. | |
| 2010/0022867 A1 | 1/2010 | Fukuchi | |
| 2010/0052958 A1* | 3/2010 | Roeven | G01R 33/3621 341/139 |
| 2011/0109315 A1 | 5/2011 | Biber et al. | |
| 2012/0249140 A1* | 10/2012 | Albsmeier | G01R 33/3692 324/309 |
| 2014/0073909 A1 | 3/2014 | Gross | |

FOREIGN PATENT DOCUMENTS

| | | |
|---|---|---|
| CN | 102053233 A | 5/2011 |
| CN | 103654782 A | 3/2014 |
| DE | 19709244 C1 | 6/1998 |
| DE | 10314215 B4 | 11/2006 |
| DE | 102009052197 B4 | 6/2013 |
| JP | H0670906 A | 3/1994 |
| JP | 2008018190 A | 1/2008 |
| KR | 20110137510 A | 12/2011 |
| KR | 101234715 B1 | 2/2013 |
| KR | 20140034090 A | 3/2014 |
| WO | WO2011159018 A2 | 12/2011 |

OTHER PUBLICATIONS

Ohinese Office Action for Chinese Application No. 201510964614.6, dated Jan. 26, 2018, with English Translation.
Korean Notice of Allowance for Korean Application No. 10-2015-0181917, dated Jul. 12, 2017.
Korean Office Action for Korean Application No. 10-2015-0181917, dated Apr. 3, 2017.

* cited by examiner

RX18, RX24, RX32, RX1, RX2, RX3:

RX18, RX24, RX32, RX1, RX2, RX3:

$M_2 < M_1$

US 10,132,885 B2

ARCHITECTURE FOR CASCADED SIGNAL SELECTION AND SIGNAL CONCENTRATION AND/OR REDUCTION OF DIGITAL RECEIVED DATA BY DECIMATION AND CHANNEL PRESELECTION

This application claims the benefit of DE 10 2014 226 676.9, filed on Dec. 19, 2014, which is hereby incorporated by reference in its entirety.

BACKGROUND

The present embodiments relate to a magnetic resonance tomography system.

Magnetic resonance devices (MRTs) for examining objects or patients using magnetic resonance tomography are known, for example, from DE 103 14 215 B4.

SUMMARY

The scope of the present invention is defined solely by the appended claims and is not affected to any degree by the statements within this summary.

The present embodiments may obviate one or more of the drawbacks or limitations in the related art. For example, a magnetic resonance tomography system is optimized.

BRIEF DESCRIPTION OF THE DRAWINGS

Further features and advantages of possible embodiments will emerge from the description of exemplary embodiments with reference to the drawing that follows, in which.

DETAILED DESCRIPTION

Figure 12:
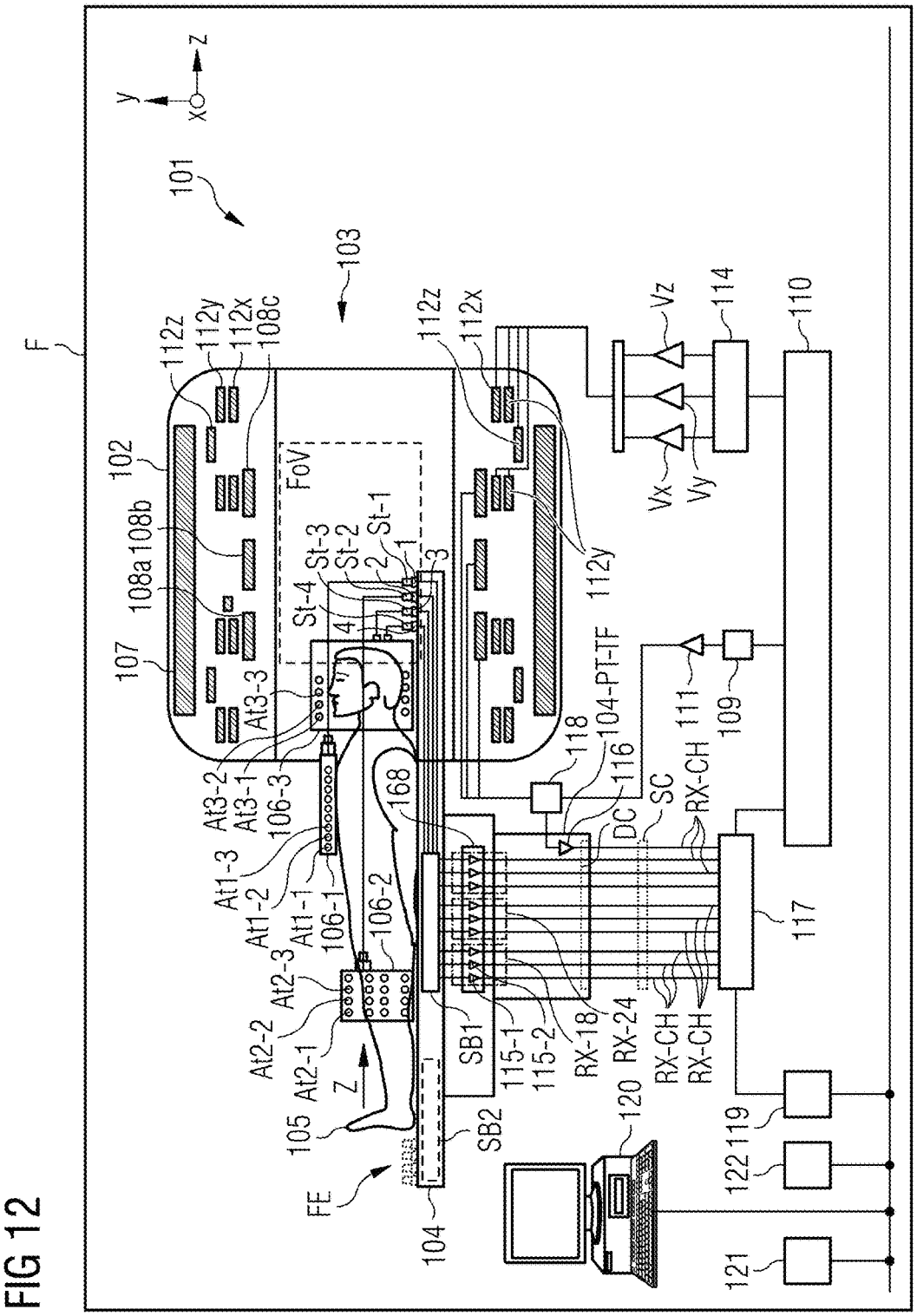
FIG. 12 shows schematically and by way of example an MRT system.

FIG. 12 shows as an overview of one embodiment of an imaging magnetic resonance device MRT 101 (e.g., located in a shielded room or Faraday cage F) including a hollow cylinder 102 having a, for example, tubular space 103 into which a patient table 104 bearing a body 105 (e.g., of an examination object such as a patient; with or without local coil arrangement 106) may be introduced in the direction of the arrow z so that images of the patient 105 may be generated by an imaging method. Disposed on the patient 105 is, for example, a local coil arrangement 106 that may be used in a local region (e.g., field of view (FoV)) of the MRT to generate images of a subregion of the body 105 in the FoV. Signals of the local coil arrangement 106 may be evaluated (e.g., converted into images, stored or displayed) by an evaluation device (e.g., including elements 168, 115, 117, 119, 120, 121, etc.) of the MRT 101 that may be connected to the local coil arrangement 106, for example, via coaxial cable or wirelessly (e.g., element 167), etc.

When a magnetic resonance device MRT 101 is used in order to examine a body 105 (e.g., an examination object or a patient) by magnetic resonance imaging, different magnetic fields that are coordinated with one another with precision in terms of temporal and spatial characteristics are radiated onto the body 105. A strong magnet (e.g., a cryomagnet 107) in a measurement chamber having, for example, a tunnel-shaped opening 103 generates a strong static main magnetic field $B_0$ ranging, for example, from 0.2 tesla to 3 tesla or more. A body 105 that is to be examined, supported on a patient table 104, is moved into a region of the main magnetic field B0 that is approximately homogeneous in the area of observation FoV. The nuclear spins of atomic nuclei of the body 105 are excited by magnetic radio-frequency excitation pulses $B1(x, y, z, t)$ that are emitted via a radio-frequency antenna (and/or a local coil arrangement if necessary) depicted in greatly simplified form as a body coil 108 (e.g., multipart body coil 108a, 108b, 108c). Radio-frequency excitation pulses are generated, for example, by a pulse generation unit 109 that is controlled by a pulse sequence control unit 110. Following amplification by a radio-frequency amplifier 111, the pulses are directed to the radio-frequency antenna 108. The radio-frequency system shown is indicated only schematically. More than one pulse generation unit 109, more than one radio-frequency amplifier 111 and a plurality of radio-frequency antennas 108 a, b, c may be used in a magnetic resonance device 101.

The magnetic resonance device 101 also has gradient coils 112x, 112y, 112z, by which magnetic gradient fields $B_G(x, y, z, t)$ are radiated in the course of a measurement in order to provoke selective layer excitation and for spatial encoding of the measurement signal. The gradient coils 112x, 112y, 112z are controlled by a gradient coil control unit 114 (and, if appropriate, via amplifiers Vx, Vy, Vz) that, like the pulse generation unit 109, is connected to the pulse sequence control unit 110.

Signals emitted by the excited nuclear spins (of the atomic nuclei in the examination object) are received by the body coil 108 and/or at least one local coil arrangement 106, amplified by assigned radio-frequency preamplifiers 116, and further processed and digitized by a receive unit and/or evaluation unit 117. The recorded measurement data is digitized and stored in the form of complex numeric values in a k-space matrix. An associated MR image may be reconstructed from the value-filled k-space matrix by a multidimensional Fourier transform. For a coil that may be operated in both transmit and receive mode (e.g., the body coil 108 or a local coil 106), correct signal forwarding is regulated by an upstream duplexer 118. From the measurement data, an image processing unit 119 generates an image that is displayed to a user via an operator console 120 and/or stored in a memory unit 121. A central computer unit 122 controls the individual system components.

FIGS. 1-12 show certain details of embodiments for cascaded analog and digital signal selection and signal concentration and reduction of digital receive data by decimation and channel preselection.

In MR tomography, images with a high signal-to-noise ratio are at present generally recorded using local coils 106-1, 106-2, 106-3 (e.g., loops). In this case, the excited nuclei induce a voltage in an antenna element (e.g., coil) of a local coil 106. The induced voltage is then amplified by a low-noise preamplifier (LNA) and forwarded by a wired connection at the MR frequency to the receive electronics. High-field systems are used to improve the signal-to-noise ratio, even with high-resolution images. The basic field strengths thereof are currently, for example, 3 tesla and higher. Since it should be possible to connect more antenna elements (e.g., loops) of local coils to an MR receiving system than there are receive signal processing elements (e.g., receivers) present, a known switch matrix (e.g., a Receive Coil Channel Selector (RCCS)) is incorporated between receive antennas and receive signal processing elements. This routes the currently active receive channels to the receive signal processing elements present. This enables more antenna elements to be connected than there are receive signal processing elements available, since in the case of whole-body coverage, the local coils that are located in the FoV or in the homogeneity volume of the magnet may be read out.

The individual antenna elements are also referred to as coil elements below. The term "coil" is also used, for example, to refer to an antenna that may include one or more antenna elements (e.g., array coil). A local coil includes, for example, antenna elements, a preamplifier, further electronics and wiring, a housing, and in most cases, at least one cable with a plug, by which the local coil is connected to the system. The term "system" or magnetic resonance tomography system 101 may be referred to as an MR system.

In known current products, there is an analog switch matrix (RCCS) that may switch any input channel to any receive signal processing element (RX). The switch matrix may, for example, be embodied as a crossbar switch. However, the current solution causes problems in systems with a very large number of channels (e.g., 128). If for example, it is desired to make 192by 128 channels freely switchable, it would thereby be possible to design an extremely large switch matrix. At high frequencies, the increasing capacity load on the line may additionally cause technical problems as the number of switches increases. Currently, known 128-channel systems are implemented by operating a plurality of identical RCCS modules in parallel.

In an MR receive system, the antenna elements (e.g., elements) are to be distributed to the individual receive signal processing elements. Since there are often more antennas on the patient than may be present simultaneously in the FoV of the magnet, fewer signal processing elements than receive antennas may be operated. For this purpose, however, a switch matrix that flexibly routes the antenna elements that may be connected to the patient table (PTAB, 104) to the receive signal processing elements present may be provided. The limited space on the front panel of PC plug-in boards represents a problem, so that when there is a larger number of receive signal processing elements, a plurality of PC plug-in boards may be necessary, simply because the space for the fiber-optic cable connections is not sufficient.

The whole switching functionality of the RCCS is currently performed in known solutions at the level of analog signals, where the digitization does not take place until later in the signal processing chain. One problem to be solved may therefore be the structural implementation and expedient spatial arrangement (e.g., low cost) of a switch matrix that processes already digitized signals beforehand.

In addition, there are solutions that implement a switching function at the patient table (e.g., SwitchBox, Essenza), as well as at analog level.

The problem of limited space on the front panel of PC plug-in cards has been solved by using a plurality of cards.

According to one embodiment, the signals (e.g., data) from antenna elements are already digitized (A/D) in at least one local coil 106-1, 106-2, 106-3 etc. or in the tabletop (e.g., a patient table tabletop or 104-PT-TT) of the patient table 104. A plurality of spatially distributed (2-16) digitization units (A/D) exist at the patient table. The plurality of spatially distributed digitization units forward the digital data (e.g., optically after an E/O conversion) to one or two central modules (e.g., at the end of the patient table tabletop PT-TT at the head end KE and/or foot end FE or in the table-foot PT-TF). There, the large data flows may be further reduced before the data flows are sent to further processing units (e.g., imagers). Examples of possible further processing steps in these one to two concentrator modules include the following.

Embodiments enable the multiple digital data flows to be combined into one data flow using a digital channel selection unit SC in order to be transmitted via a transmission medium LWL (e.g., a glass or plastic fiber) to the system 117, 101. This embodiment is advantageous because a coverable patient table may be used. The coverable patient table is then to be fitted with optical connectors. These may be embodied as a fiber-lens-lens-fiber combination and because of the optical components and the precision are expensive. Hence, the aim is to keep the number of these components low.

The combination results in two data flows at X1 and X2 GBit/s becoming, for example, one new data flow at X3=X1+X2 GBit/s. In one embodiment, for example, only the data flows that are required for the MR experiment and were selected by the controller are selected for further transmission. As a result, a preselection of the connectable channels to the channels actually to be processed is implemented (e.g., digital switch matrix). A reduction by selection may be provided.

Embodiments relate, for example, to a reduction in the data flow by data decimation using a decimation filter (e.g., a bandpass or lowpass decimation filter (reference character: Decimation)).

Possibilities include a reduction by filtering, a combination of concentration, decimation and selection in one module or even in the same logical operation as shown herewith.

Embodiments may, for example, also relate to one or two of the following aspects.

1. Cascading of an analog and a digital channel selection level for the gradual reduction in the signals to be transmitted between local coils and imagers—possibly already in the patient table to reduce the connection system costs in the case of coverable tables.
2. Use of a digital signal concentration unit that combines several digital RX outputs and performs a channel selection and possibly a further data rate decimation (e.g., data reduction). The cost of a receive chain may be optimized.

Figure 1:
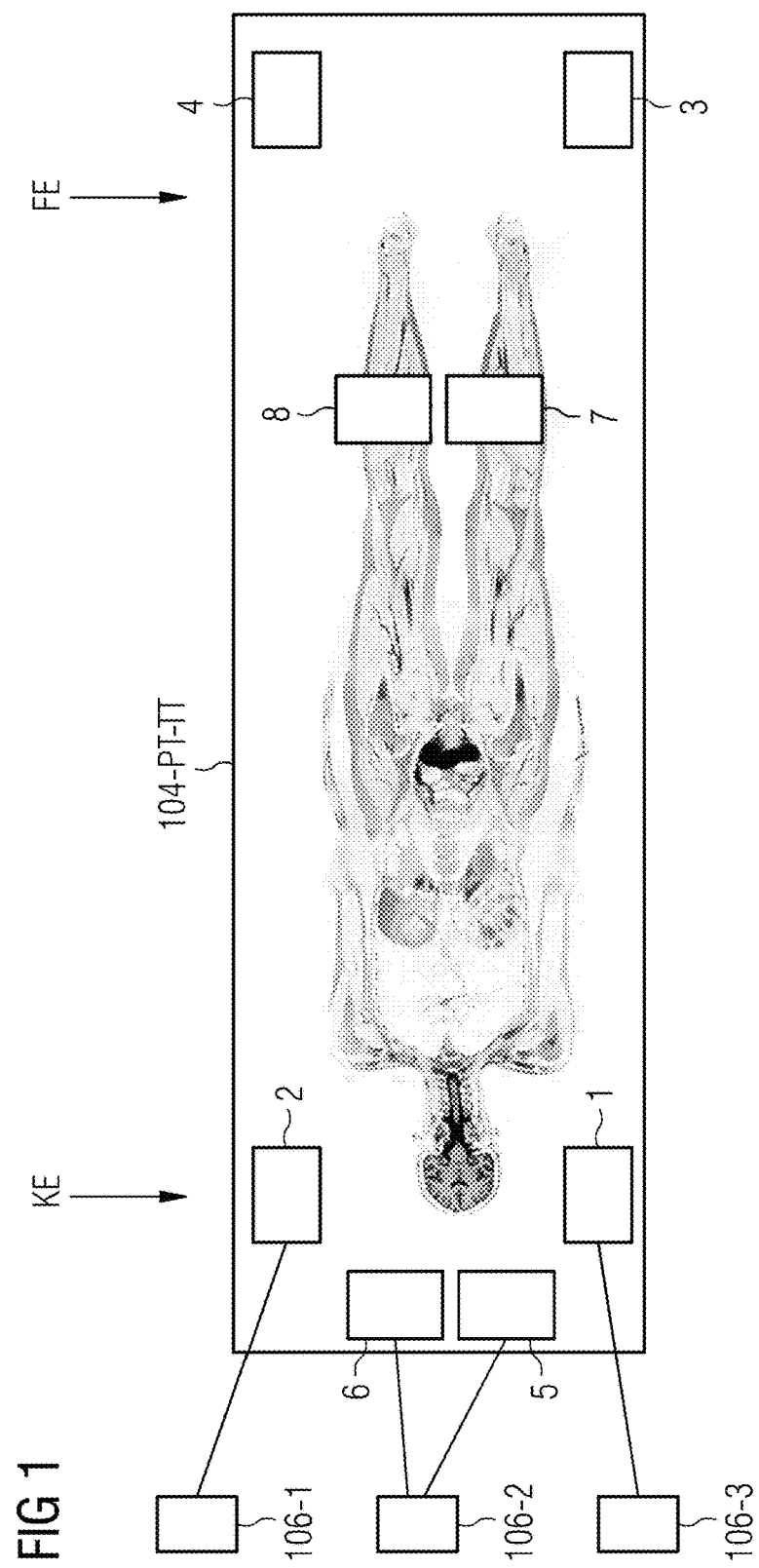
FIG. 1 shows schematically and in simplified form by way of example a top view of a patient table.

FIG. 1 shows schematically and in simplified form a top view of one embodiment of a patient table tabletop 104-PT-TT of a patient table 104 with a plurality of MRT plugs 1, 2, 5, 6; 3, 4, 7, 8. The plurality of MRT plugs 1, 2, 5, 6; 3, 4, 7, 8 are at a head end KE and at a foot end FE, respectively, for the respective connection of a local coil 106-1, 106-2, 106-3 to the MRT plugs 1, 2, 5, 6; 3, 4, 7, 8 (e.g., three local coils 106-1, 106-2, 106-3 at the head end of the patient table tabletop 104-PT-TT).

Figure 2:
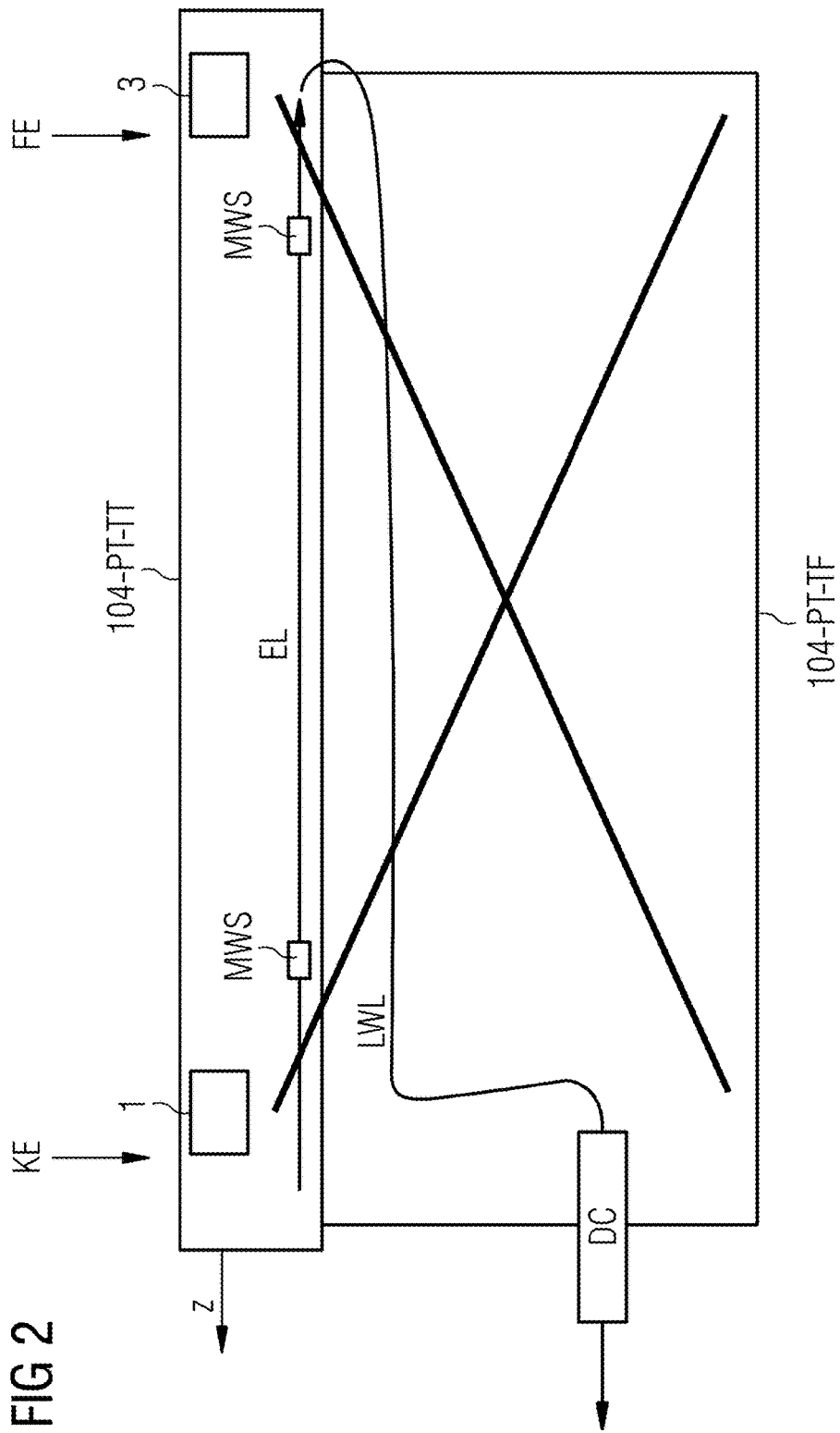
FIG. 2 shows schematically and in simplified form in cross-section by way of example a patient table.

FIG. 2 shows schematically and in simplified form in cross-section one embodiment of a patient table tabletop 104-PT-TT of a patient table 104 with, at the head end KE and at the foot end FE, respectively, a plurality of MRT plugs 1; 3 for the respective connection of a local coil to the MRT plugs. Signal paths (e.g., with electrical cables EL and/or optical cables LWL) are provided through the patient table tabletop 104-PT-TT of the patient table, the patient table table-foot PT-TF of the patient table, and a docking station DC, and onward to an evaluation unit 117, 110, 120 of the MRT 101 (not shown in FIG. 2).

Figure 3:
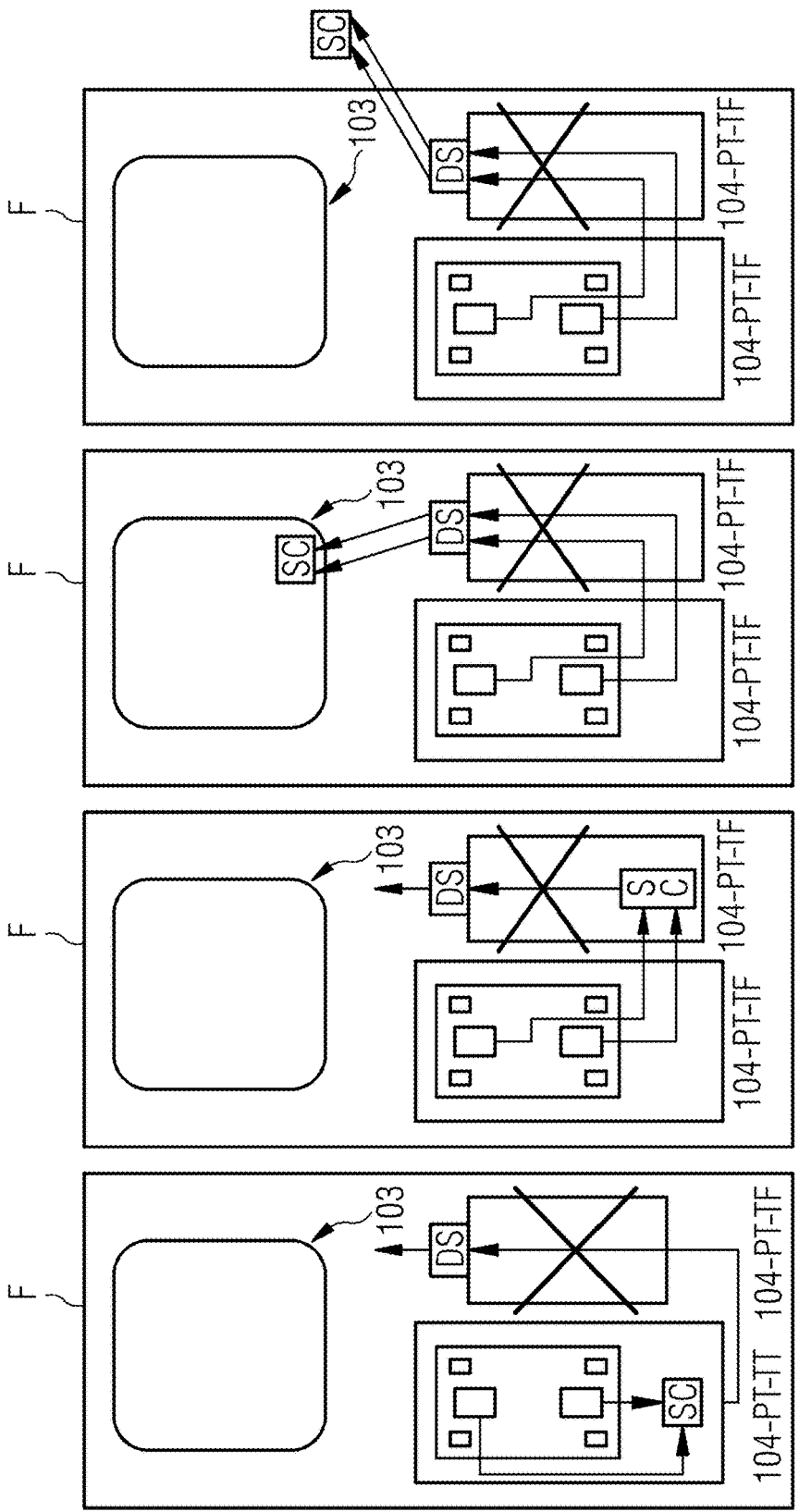
FIGS. 3A, 3B, 3C, and 3D show schematically and in simplified form next to one another by way of example four variants of the spatial arrangement of a digital channel selection unit.

FIG. 3 shows schematically and in simplified form next to one another by way of example four variants FIG. 3a, FIG. 3b, FIG. 3c, FIG. 3d of the signal paths and of the spatial arrangement of a digital channel selection unit SC. The digital channel selection unit SC is for digital channel selection after an analog channel selection SB1, SB2 for a selection of the signals of some or all antenna elements (e.g., only some of the local coils (106-1, 106-2, 106-3, 106-4) and/or MRT plugs 1, 2, 5, 6; 3, 4, 7, 8); in FIG. 3a, in the patient table tabletop 104-PT-TT, in FIG. 3b, in the patient table table-foot PT-TF, in FIG. 3c, in the MRT bore 103, and in FIG. 3d, in a technical room outside the shielded room F).

Figure 4:
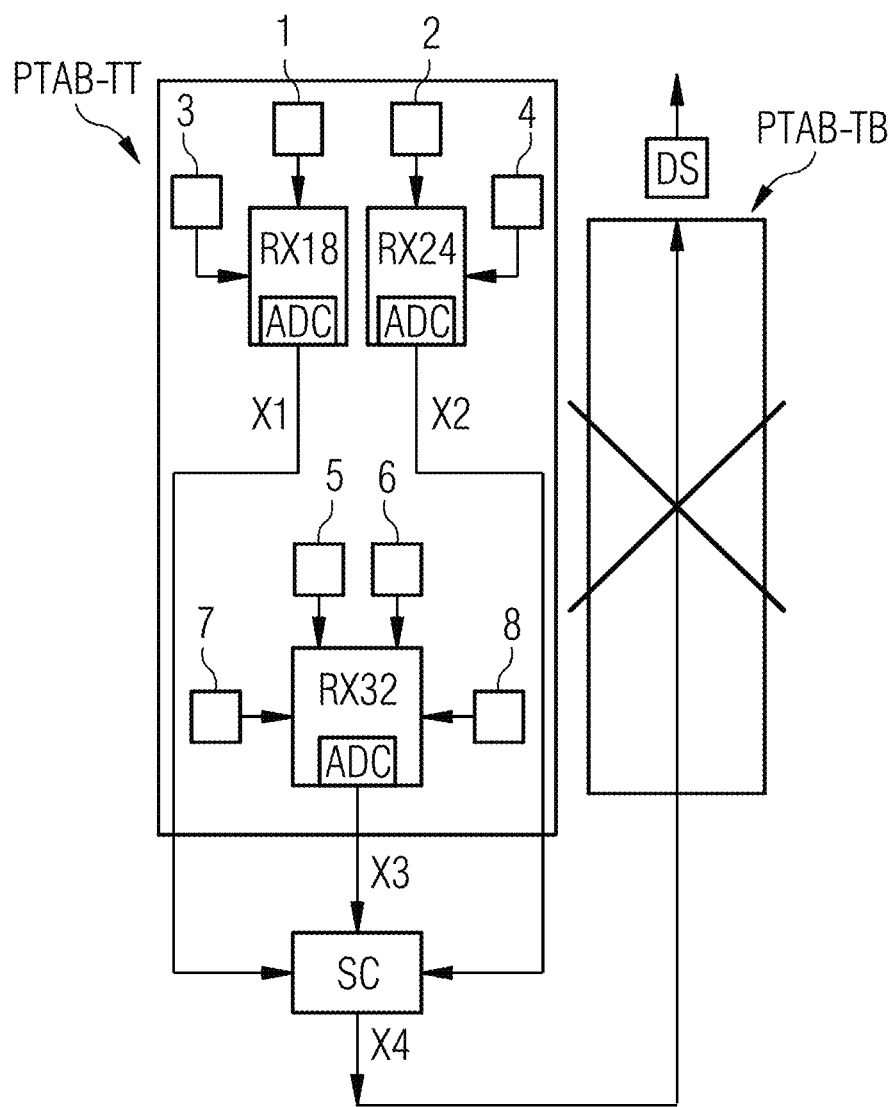
FIG. 4 shows schematically and in simplified form by way of example a top view of signal paths from MRT plugs to a docking station of the patient table.

FIG. 4 shows schematically and in simplified form by way of example a top view of exemplary signal paths X1, X2, X3, X4 from MRT plugs 1, 2, 3, 4, 5, 6, 7, 8 to a docking station DS of the patient table 104 through patient table tabletop 104-PT-TT and in the patient table table-foot PT-TF.

Figure 5:
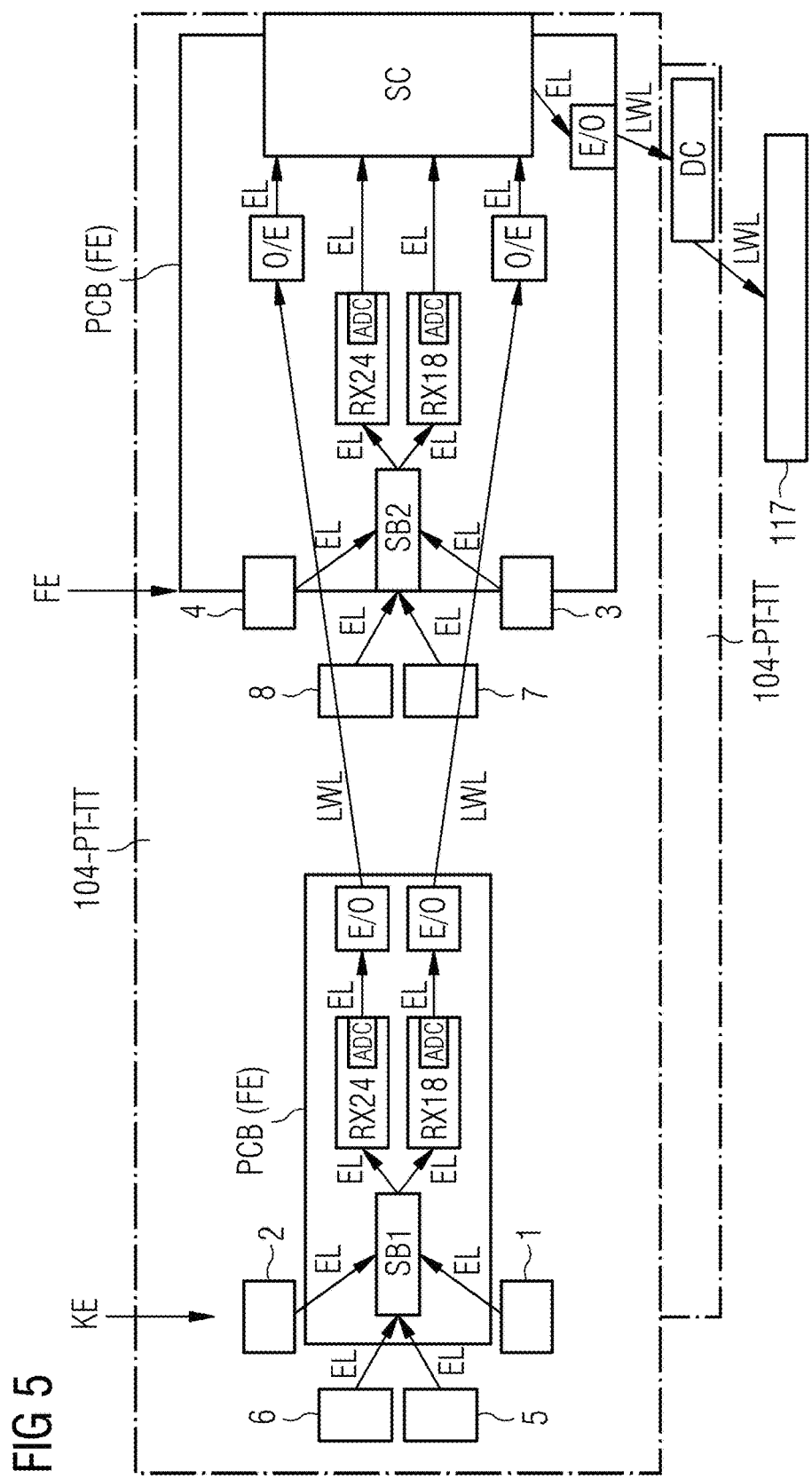
FIG. 5 shows schematically and in simplified form by way of example a top view of signal paths for signals from MRT plugs onward to an evaluation unit.

FIG. 5 shows schematically and in simplified form by way of example a top view, in the event of a digital channel selection unit (SC) being disposed at the foot end FE in the patient table tabletop 104-PT-TT or the patient table table-foot PT-TF: optical (e.g., fiber-optic cables LWL) and electrical (e.g., electrical cables EL) signal paths for signals from MRT plugs (e.g., for local coils) at the head end KE and at the foot end FE, respectively, via an analog channel selection unit SB1, SB2 for an analog channel selection, a digital channel selection unit (SC) for a digital channel selection, a docking station of the patient table onward to an evaluation unit 117 of the MRT 101 (e.g., with electro-optic converters (E/O) for conversion of electrical into optical signals and opto-electric converters (O/E) for conversion of optical into electrical signals being provided in signal paths).

Figure 6:
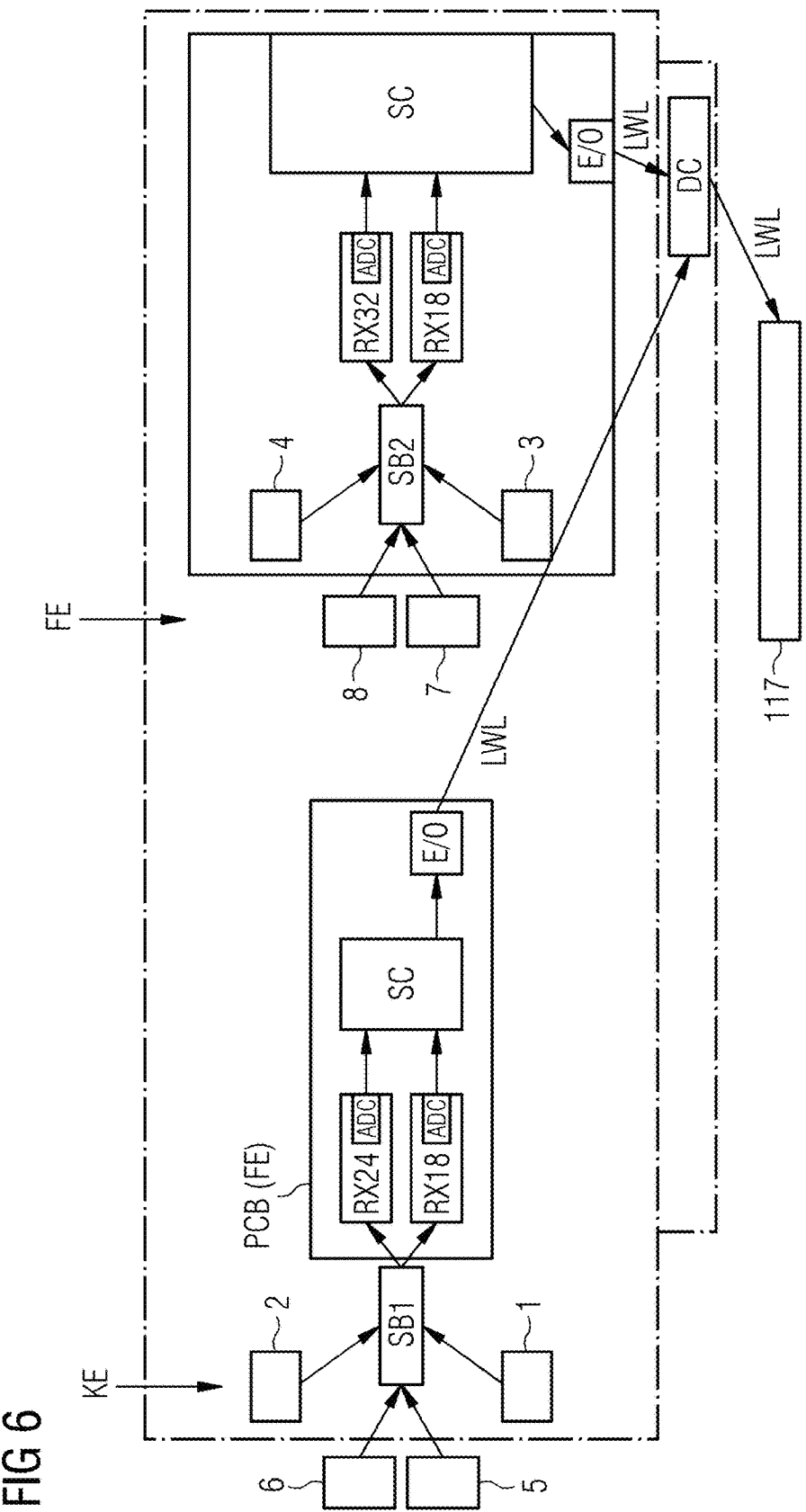
FIG. 6 shows schematically and in simplified form by way of example a top view of signal paths for signals from MRT plugs onward to an evaluation unit.

FIG. 6 shows schematically and in simplified form a top view by way of example of one embodiment of a digital channel selection unit (SC) disposed in the patient table tabletop 104-PT-TT or patient table table-foot PT-TF. Optical (e.g., fiber-optic cables LWL) and/or electrical (e.g., electrical cables EL) signal paths for signals are provided from MRT plugs (or local coils) at the head end KE and at the foot end FE, respectively, via an analog channel selection unit SB1, SB2 for an analog channel selection, a digital channel selection unit (SC) for a digital channel selection, a docking station DC of the patient table onward to an evaluation unit 117 of the MRT 101 (e.g., with electro-optic converters (E/O) for conversion of electrical into optical signals and opto-electric converters (O/E) for conversion of optical into electrical signals being provided in signal paths).

In contrast to FIG. 5, in FIG. 6, the signals selected by an analog channel selection unit SB1 at the head end are not, as in FIG. 5, forwarded to a digital channel selection unit (SC) for a subsequent (e.g., subsequent to the analog selection) digital channel selection, but are direct to a docking station.

Figure 7:
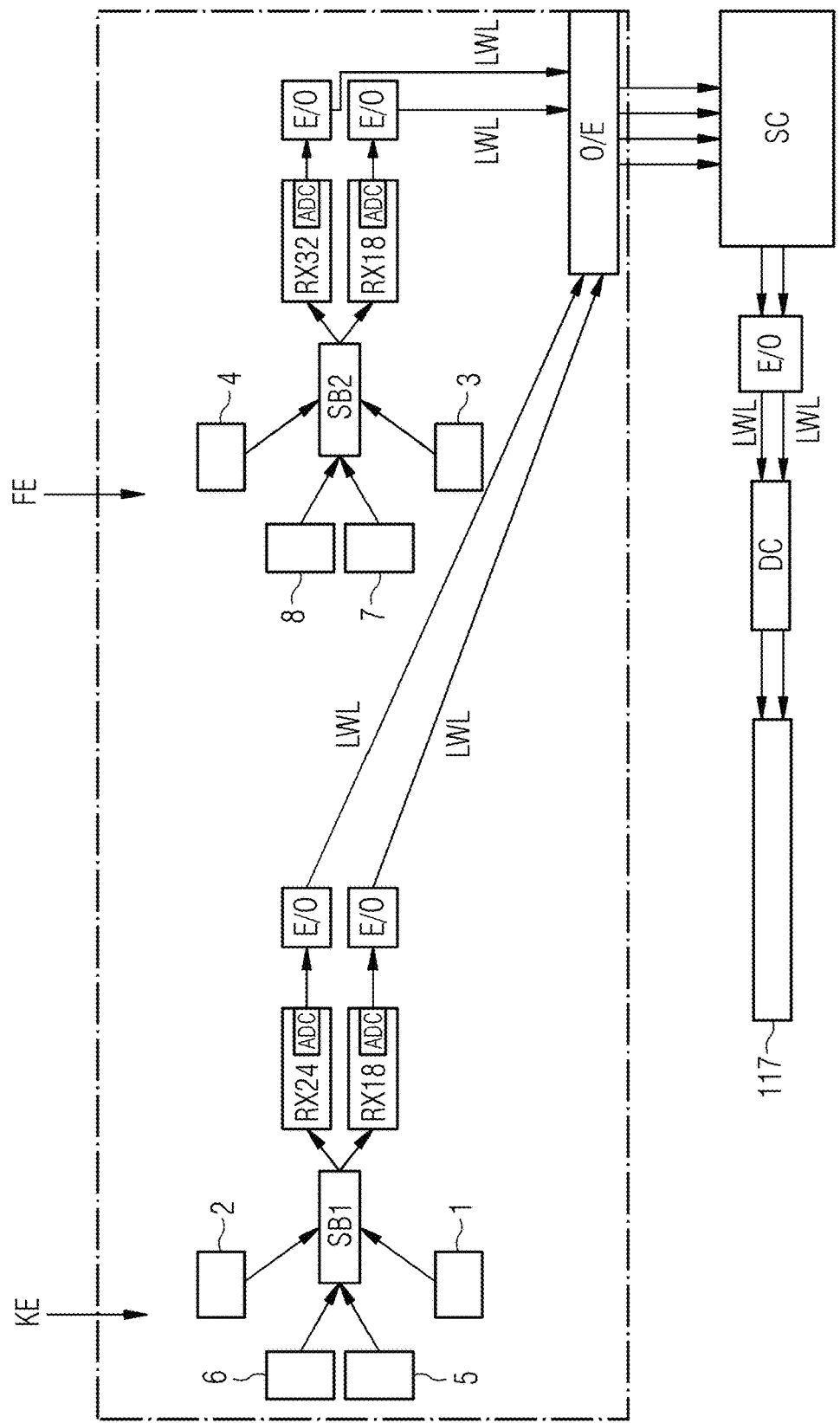
FIG. 7 shows schematically and in simplified form by way of example a top view of signal paths for signals from MRT plugs onward to an evaluation unit.

In FIG. 7, at a digital channel selection unit (SC) disposed, for example, at the bore 103, signals from MRT plugs (e.g., for local coils/antenna elements) at the head end KE and at the foot end FE are respectively forwarded to an analog channel selection unit SB1, SB2 (e.g., and from the digital channel selection unit (SC) disposed at the bore 103, are passed to a docking station of the patient table and onward to an evaluation unit 117).

Figure 8:
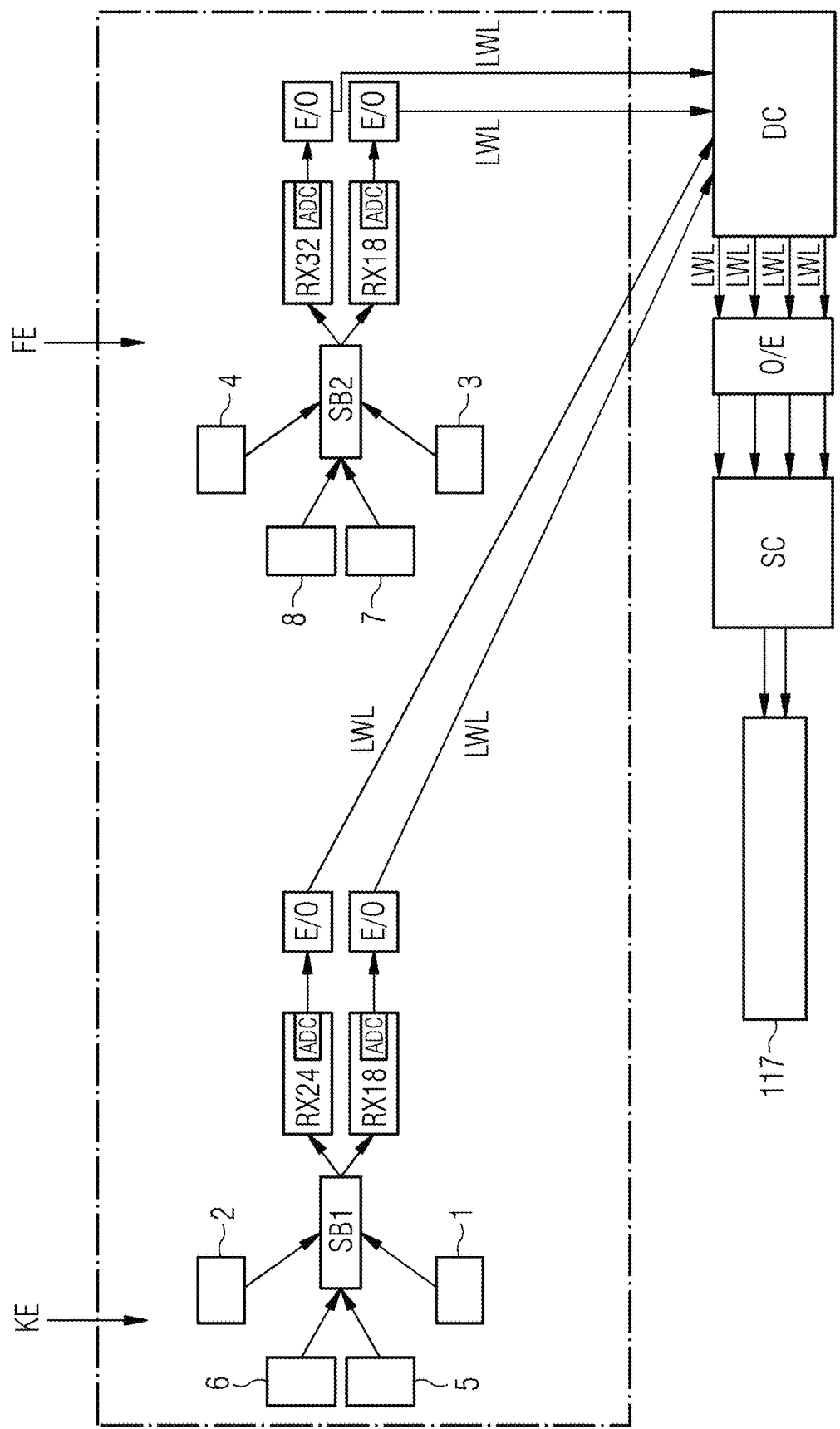
FIG. 8 shows schematically and in simplified form by way of example a top view of signal paths for signals from MRT plugs onward to an evaluation unit.

In FIG. 8, one embodiment of a digital channel selection unit SC disposed, for example, in a technical room (e.g., outside the FoV) is provided in signal paths for signals from MRT plugs (e.g., for local coils/antenna elements) at the head end and at the foot end to an evaluation unit 117.

Figure 9A:
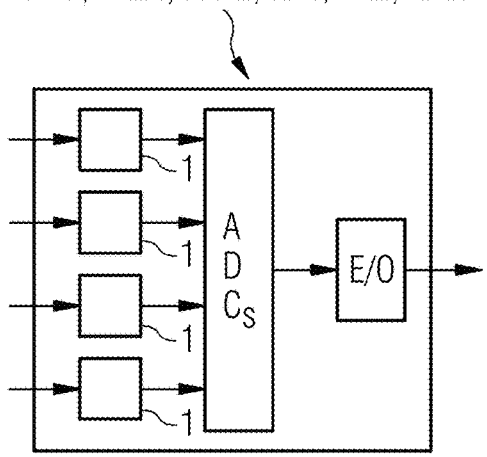
FIGS. 9A and 9B show schematically and in simplified form two examples of details of receive signal processing element blocks.
Figure 9B:
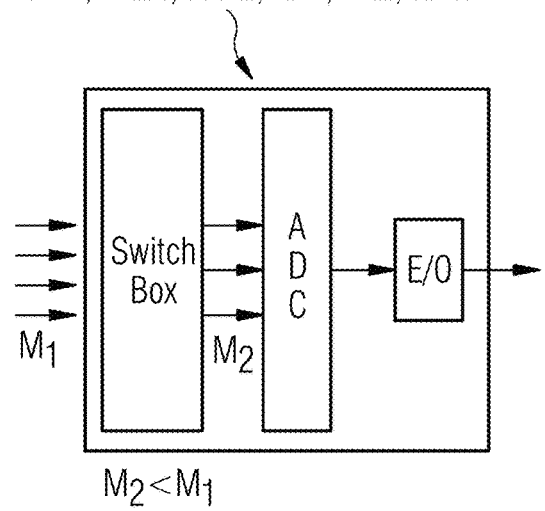

FIGS. 9a and 9b show schematically and in simplified form two examples of certain details of receive signal processing element blocks (e.g., RX18, RX24, RX32, RX1, RX2, RX3) with an electro-optic converter (E/O)). Each of the receive signal processing element blocks has a plurality of receive signal processing elements (RX-CH) with an analog/digital converter (ADC), and on the left without and on the right with an analog sampling unit (e.g., SwitchBox) in the receive signal processing element block (e.g., RX18, RX24, RX32, RX1, RX2, RX3) for channel reduction from M1 analog signals to M2 (e.g., M2<M1) analog signals.

Figure 10:
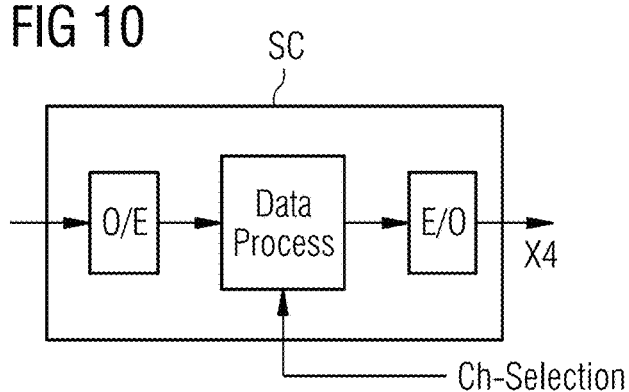
FIG. 10 shows one embodiment of a digital channel selection unit.

FIG. 10 shows one embodiment of a digital channel selection unit SC with an opto-electric converter (O/E), an electro-optic converter (E/O), and a sampling and selection device (DataProcess). The digital channel selection unit SC, on the input side, may be connected to antenna elements (e.g., At1-1 . . . At1-3, At2-1 . . . At2-3, At3-1 . . . At3-3) and therefrom, in accordance with a selection signal (e.g., CH-selection), selects signals of fewer than all antenna elements (e.g., At1-1 . . . At1-3, At2-1 . . . At2-3, At3-1 . . . At3-3). On the output side (X4) of the digital channel selection unit SC, the digital channel selection unit SC emits in the direction of an evaluation unit (117).

Figure 11:
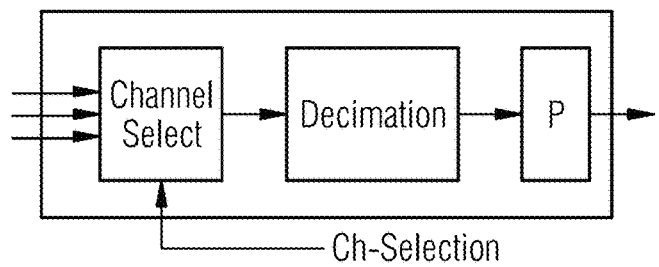
FIG. 11 shows one embodiment of a sampling and selection device similar to the device shown in FIG. 10.

FIG. 11 shows a sampling and selection device (e.g., DataProcess) similar to that in FIG. 10. The sampling and selection device also has a signal compression unit (e.g., decimation) for data reduction by, for example, compression or recoding or highpass/lowpass.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography system comprising:
a plurality of magnetic resonance tomography (MRT) plugs for connection of respective antenna elements of one of a plurality of local coils;
at least one analog switch matrix, due to which antenna elements respectively connected to fewer than all of the MRT plugs are connectable in an analog fashion to receive signal processing elements of one of a plurality of receive signal processing element blocks respectively having a plurality of receive signal processing elements;
an evaluation device; and
a digital channel selection unit provided between outputs of the receive signal processing element blocks and the evaluation device, the digital channel selection unit, on an input side, being connectable to the antenna elements,
wherein signals from fewer antenna elements are present at the output of the digital channel selection unit than at the input of the digital channel selection unit.

2. The magnetic resonance tomography system of claim 1, wherein fewer receive signal processing element blocks than MRT plugs are provided.

3. The magnetic resonance tomography system of claim 1, wherein outputs from the receive signal processing element blocks are switched via one or more electro-optic converters and via at least one digital channel selection unit to at least one fiber-optic cable, a signal compression unit with or without other interposed elements being connectable to the evaluation device.

4. The magnetic resonance tomography system of claim 1, further comprising analog/digital converters connectable to antenna elements of a local coil disposed in the local coil.

5. The magnetic resonance tomography system of claim 4, wherein the analog/digital converters are disposed in a patient table.

6. The magnetic resonance tomography system of the claim 1, wherein the receive signal processing element blocks each have one or more analog/digital converters connected upstream of precisely one electro-optic converter, for signals from respectively one of the antenna elements, and
wherein signals at the output of an analog/digital converter respectively have different light frequencies to transmit the signals collectively via a common fiber-optic cable.

7. The magnetic resonance tomography system of claim 1, further comprising a plurality of opto-electric converters connected upstream of a signal compression unit, to which one of the outputs of one of the receive signal processing element blocks is connected via an electro-optic converter and at least one fiber-optic cable.

8. The magnetic resonance tomography system of claim 1, further comprising a signal compression unit, the signal compression unit comprising:
a channel selection device that is actuatable by a selection signal; and
precisely one or precisely two electro-optic converters connected downstream of the channel selection device.

9. The magnetic resonance tomography system of claim 1, wherein a channel selection device has a signal compression unit connected downstream of the channel selection device, which is actuatable by a selection signal.

10. The magnetic resonance tomography system of claim 1, wherein at a head end of a patient table, a first subset of MRT plugs of a plurality of MRT plugs are provided for connection of antenna elements, respectively, of one of a plurality of local coils,
wherein due to a first switch matrix, antenna elements, connected to fewer than all of the first subset of MRT plugs, of local coils are switchable to receive signal processing elements of one of the plurality of receive signal processing element blocks having, respectively, a plurality of receive signal processing elements with at least digital/analog converters,
wherein at a foot end of the patient table, a second subset of MRT plugs of the plurality of MRT plugs are provided for connection of antenna elements, respectively, of another of the plurality of local coils, and
wherein due to a second switch matrix, antenna elements, connected to fewer than all of the second subset of MRT plugs, of local coils are switchable to receive signal processing elements of one of the plurality of receive signal processing element blocks having, respectively, a plurality of receive signal processing elements with at least digital/analog converters.

11. The magnetic resonance tomography system of claim 1, wherein some or all of the MRT plugs are MRT plugs mounted on a patient table.

12. The magnetic resonance tomography system of claim 11, wherein some or all of the MRT plugs are MRT plugs mounted at a head end, a foot end, or the head end and the foot end of a patient table.

13. The magnetic resonance tomography system of claim 1, wherein MRT plugs mounted at a head end of a patient table and MRT plugs mounted at a foot end of the patient table are switchable to a same patient table MRT docking connector via a fiber-optic cable, respectively.

14. The magnetic resonance tomography system of claim 1, further comprising an electro-optic converter connected upstream of a patient table MRT docking connector between a patient table and the magnetic resonance tomography system,
wherein at least one fiber-optic cable is connected downstream.

15. The magnetic resonance tomography system of claim 1, wherein a patient table MRT docking connector is disposed between a patient table and the magnetic resonance tomography system in a foot underneath a table of the patient table.

16. The magnetic resonance tomography system of claim 1, wherein MRT plugs mounted at a head end of a patient table and MRT plugs mounted at a foot end of the patient table are switchable to a same electro-optic converter via a fiber-optic cable, respectively.

17. The magnetic resonance tomography system of claim 1, wherein MRT plugs mounted at a head end of a patient table and MRT plugs mounted at a foot end of the patient table are switchable to a same signal compression unit via one connection, respectively.

18. The magnetic resonance tomography system of claim 17, wherein the same signal compression unit is switched to an electro-optic converter, which is switched to patient table MRT docking connectors.

19. The magnetic resonance tomography system of claim 1, wherein an output of one or a plurality of receive signal processing element blocks is switched to precisely one signal compression unit at a head end of a patient table, respectively, via an electro-optic converter and a fiber-optic cable,
wherein an output of one or a plurality of receive signal processing element blocks at a foot end of the patient table is connected to the one signal compression unit via, respectively, an electro-optic converter and a fiber-optic cable, and wherein the one signal compression unit is connectable to an evaluation device of the magnetic resonance tomography system.

20. The magnetic resonance tomography system of claim 1, further comprising a signal compression unit, the signal compression unit being disposed in a patient table tabletop of a patient table, in a patient table-foot of the patient table, or in a housing of a bore or outside a shielded Faraday cage of the magnetic resonance tomography system.

* * * * *